United States Patent [19]

Gerson

[11] Patent Number: 5,033,321
[45] Date of Patent: Jul. 23, 1991

[54] METHOD AND APPARATUS FOR MEASURING THE DEGREE OF MIXING IN A TURBULENT LIQUID SYSTEM

[76] Inventor: Donald F. Gerson, 208 Kennedy St. West, Aurora, Ontario L4G 2L7, Canada

[21] Appl. No.: 394,575

[22] Filed: Aug. 16, 1989

[30] Foreign Application Priority Data

Aug. 16, 1988 [CA] Canada .................................. 574875

[51] Int. Cl.$^5$ ............................................. G01N 33/00
[52] U.S. Cl. ........................................ 73/866; 73/53; 137/3
[58] Field of Search .................... 73/53, 61 R, 61.1 R, 73/866; 137/3, 88; 366/142; 374/147

[56] References Cited

U.S. PATENT DOCUMENTS

| | | | |
|---|---|---|---|
| 3,841,144 | 10/1974 | Baldwin | 73/61 R |
| 4,049,012 | 9/1977 | Van de Kooi | 137/88 X |
| 4,415,408 | 11/1983 | Greey | 73/61 R X |
| 4,436,429 | 3/1984 | Strong et al. | 366/142 X |
| 4,527,420 | 7/1985 | Foote | 73/61 R |
| 4,679,426 | 7/1987 | Fuller et al. | 73/61 R X |
| 4,693,415 | 9/1987 | Sturm | 137/88 X |
| 4,774,680 | 9/1988 | Agar | 73/61.1 R X |
| 4,801,863 | 1/1989 | Schimion et al. | 73/61.1 R X |

FOREIGN PATENT DOCUMENTS 783905 4/1968 Canada .

OTHER PUBLICATIONS

L. J. Leggat & N. C. Sponagle, Journal of Fluids Engineering, vol. 107, pp. 127-133, (Mar. 1985).
T. E. Siddon, Flow, vol. 1, pt. 1, pp. 435-439, (1974).
M. Cartwright, New Scientist, pp. 12-14, (May 9, 1985).
D. F. Gerson, European J. Appl. Microbiol. Biotechnol., vol. 10, pp. 59-72, (1980).
M. A. Rao & R. S. Brodkey, Chemical Engineering Science, vol. 27, pp. 137-156, (1972).

*Primary Examiner*—Hezron E. Williams
*Assistant Examiner*—Joseph W. Roskos
*Attorney, Agent, or Firm*—Elman & Wilf

[57] ABSTRACT

A method and apparatus are disclosed for measuring the degree or rate of mixing in a turbulent liquid system. The method involves inserting into the liquid system a probe capable of responding to variations in a chemical or physical parameter which can vary in the system, e.g. pressure, velocity, acceleration, pH value, conductivity or temperature. A signal from the probe indicating the parameter is processed by transforming it to a readable electronic output and this output is then compared with a calibrated range so as to enable the mixing process to be monitored or optimized.

22 Claims, 2 Drawing Sheets

METHOD AND APPARATUS FOR MEASURING THE DEGREE OF MIXING IN A TURBULENT LIQUID SYSTEM

This invention relates to a method of measuring the degree or rate of mixing in liquids.

Mixing is an important aspect of many commercial processes involving liquids and solutions. The rates of chemical and physicochemical processes in liquids are generally dependent on the degree or efficiency of mixing in the reaction medium. Liquid mixing equipment is integral to the chemical and food processing industries. Liquid mixing devices of many designs have been constructed and are presently in use. The choice and operational characteristics of a liquid mixing device are usually based on consideration of the power consumption of the device during normal operating conditions. This parameter is usually used because it relates to an easily measured quantity (e.g. electrical current) and because the cost of power is an important economic consideration in industry. However, power consumption considers only the input to the liquid system being mixed and does not measure the ultimate behaviour of the liquid in relation to the mixing process.

Mixing is commonly associated with turbulent flow in fluids, and it is generally assumed that achievement of turbulence is sufficient to provide a "well mixed" condition. It has not previously been practical to quantitate the degree of turbulence. However, numerous attempts have been made to characterize turbulence and the most generally successful approach is to use measurements of the power spectrum as a "fingerprint" for the degree of turbulence in a particular environment. This approach is most commonly used to characterize turbulence encountered in wind tunnel studies of aircraft or in boundary layer wind tunnel studies of air flow around buildings.

Applications of the power spectrum most commonly involve measurement of fluctuations in the velocity of fluid flowing around an object of study. A time series of these fluctuations over a specified time period may be transformed by Fourier Analysis into a graph of either intensity or power against a wide range of frequencies. This graph is referred to as the power spectrum and is used to determine and characterize the turbulence associated with the object under study under specified conditions.

Attempts have been made to extend the use of the power spectrum to the study of turbulence in liquids. M. A. Rao and R. S. Brodkey (Chem. Engr. Sci., Vol. 27 pp. 137-156, 1972) studied the power spectra of variations in the velocity of liquid flow in a stirred chemical reactor and attempted to relate aspects of the spectrum to eddy sizes and the rate of rotation of the mixing impeller. In Canadian Patent No. 783,905, H. S. Ribner and T. E. Siddon describe a method and means of measuring velocity fluctuations in unsteady flow, which comprises a sensor device which could be used to characterize the turbulence of flowing fluids, and T. E. Siddon used such a device to produce a power spectrum of turbulent liquid flow as described in H. W. Stoll, Flow, Vol. 1, Instrument Society of America, 1974. L. J. Leggat and N. C. Sponagle, Journal of Fluids Engineering, Vol 107, page 127, 1985, have used measurements of the power spectrum to characterize the sounds of cavitation produced by various propellers.

In all cases, relatively high frequencies ranging from the high kilohertz range down to the 1-10 hertz range have been used. The only report relating power spectral information to the consequences of mixing in stirred reactors relates the power spectrum to oil-water emulsification (D. F. Gerson, Eur. J. Appl. Microbiol. Biotechnol. Vol. 10, p. 5972, 1980). That study is distinguished from the present invention since it describes an equilibrium mechanical process rather than the rate of a chemical or physicochemical process. In addition, at that time it had not been discovered that particular bands of the power spectrum could be correlated with the rate of chemical or physicochemical processes.

It is an object of the invention to provide an improved method of measuring the degree of mixing in turbulent liquid systems and, hence, the rate of chemical or physicochemical reactions therein.

Accordingly, one aspect of the invention provides a method of measuring the degree of mixing in a turbulent liquid system, which comprises:

(a) inserting into the liquid system a probe capable of responding to variations in a chemical or physical parameter which can vary in said system, (b) electronically processing a signal from said probe by transforming said signal to readable output, and (c) comparing said output with a calibrated range so as to enable the mixing process to be monitored or optimized.

Another aspect of the invention provides an apparatus for measuring the degree of mixing in a turbulent liquid system, which comprises:

(a) probe means capable of responding to variations in a chemical or physical parameter in a liquid system, (b) processing means for electronically transforming a signal from said probe to a readable output, (c) display means for displaying a readable output obtained from said processing means, and (d) means for comparing said output with a calibrated range for monitoring or optimizing mixing or reaction conditions in the liquid system.

Thus, the present invention broadly relates to the measurement of the degree of mixing that is actually occurring in the liquid by the use of a probe that is inserted into the liquid. The method embodied in this invention allows direct measurement of the components of the liquid motion which are related to the rates of chemical or physicochemical reactions of interest to industries requiring liquid mixing. Measurement of a parameter which relates more precisely to the desired result of the mixing will allow more careful optimization of mixing processes with consequent improvements in the cost of operating mixing equipment and the efficiency of the process requiring mixing. In effect, the method measures mixing as it relates to a given process fluid under operating conditions.

Thus, the present invention provides a method for measuring the mixing in turbulent liquid systems which relates to the rates of chemical and physicochemical reactions or processes. The measurement method provides a numerical output, termed the mixing signal, which relates to those aspects of the turbulence which contribute to the enhancement of the rate of the reaction taking place in the process. One aspect of the invention involves the insertion of a probe into a stirred reaction vessel. The probe reports variations in, for instance, either pressure or velocity to an electronic apparatus which separates out that part of the power spectrum relevant to increasing the rate of the subject process, and converts that segment of the power spectrum to a mixing signal with a particular numerical value. The mixing signal is proportional to the degree of mixing and can be used by the operator of the mixing equipment to optimize the rate or cost of the process. While prior art has defined general measurement systems for obtaining the power spectrum of turbulent fluid systems, the key components of the power spectrum which relate to the rates of chemical and physicochemical reactions have not previously been isolated. A need exists for a measurement method of general utility in commercial processes involving mixing.

The method generally involves the following components and steps:

(a) A probe is required which responds to variations in a chemical or physical parameter which can be affected by the mixing process. Examples include probes for pressure, velocity, acceleration, chemical concentration (e.g. pH or conductivity) or temperature. The probe must have a response time such that it will accurately respond to variations within an appropriate subset of the frequency range of 0.01 Hz to 10 MHz.

(b) An electronic apparatus which will perform the following functions in aggregate:

(1) amplifying the signal from the probe;

(2) filtering the signal from the probe to remove unwanted frequency ranges, a minimum configuration would include at least one high pass filter (cutoff frequencies 0.001 to 1.0 Hz) and one low pass filter (cutoff frequencies 10 Hz to 10 MHz);

(3) signal processing which reduces the filtered signal either to a power spectrum over a specified frequency range or to a transformed single numerical output (e.g. RMS, logRMS, RMS of the log of the filtered signal, or another summarizing transformation), termed the mixing signal; and (4) output signal conditioning which produces a display of the resultant signal or a voltage or current output appropriate to the input of a recording device or computer.

(c) A calibration process which involves the use of the relevant process to select the appropriate frequency range or ranges which correlate with the rate of the process.

(d) The use of the apparatus and method to monitor and optimize the mixing process. In particular, it has been discovered that for processes involving the most common types of stirred, baffled reactors, the frequency range which is most relevant to the rate of chemical or physicochemical reactions, such as the dissolution of oxygen in water or to chemical reactions, is between 0.01 Hz and 1000 Hz.

Embodiments of the invention will now be described, by way of example, with reference to the accompanying drawings, in which:

FIG. 2b is a diagrammatic sectional view of a probe for use in the device of FIG. 2a.

Figure 1A:
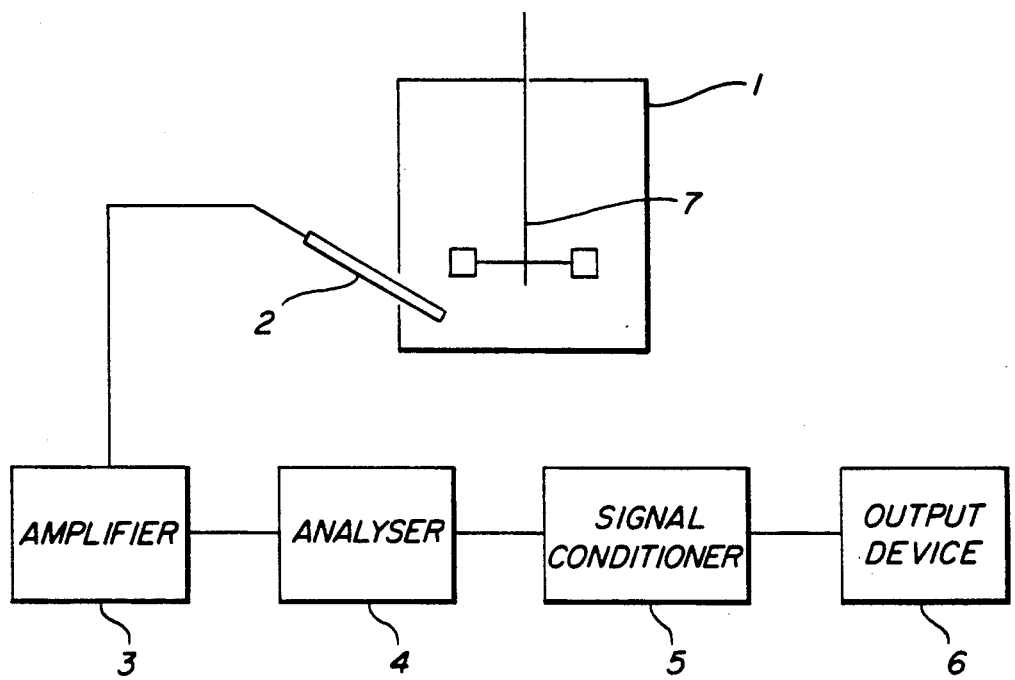
FIG. 1a is a block diagram of an apparatus for measuring the degree of mixing in a liquid system.
Figure 1B:
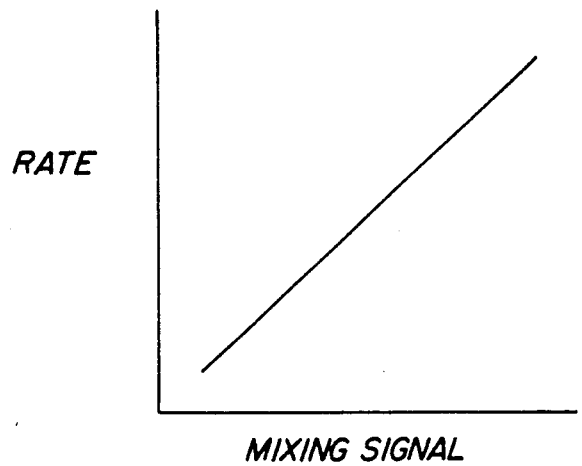
FIG. 1b shows graphically the type of relationship expected between the output of the apparatus (mixing signal) and the reaction rate of the process.

An embodiment of apparatus which is useful in the present invention is depicted in FIG. 1a and FIG. 1b. FIG. 1a is a block diagram of the apparatus, comprising a mixing tank 1, a probe 2, an amplifier 3, an analyser 4, a signal conditioner 5 and an output device 6. FIG. 1b shows the type of relationship expected between the output of the apparatus (mixing signal) and the rate of the process. Typically, the process will take place in a chemical reactor consisting of the tank 1 with a mechanically driven mixer 7, most commonly a propeller or impeller on a motor-driven shaft. The probe 2 is inserted into the liquid either from the surface of the liquid or from a port in the side of the tank. A preferred type of probe is a sealed pressure or acceleration probe which will neither interfere with nor be damaged by the liquid or other components of the process and which is adapted to measurements at the frequencies in the relevant range. The electrical output of the probe is then fed into the electronic apparatus for processing. From the probe the signal is first amplified in the amplifier 3, then electronically filtered to restrict the frequency range to a specified band or bands within the range of from 0.01 to 1000 Hz. The filtered signal is then fed into the signal analysis module 4 which has as output mixing signal the RMS signal over this frequency range. FIG. 1b shows graphically the rate of the process being mixed in relation to the mixing signal from the apparatus of FIG. 1a.

The following Examples illustrate the invention.

EXAMPLE 1:

This example relates to determination of the relationship between aeration rate and oxygen dissolution rate in a gassed chemical reactor. A chemical reactor with an internal diameter of 15 cm was studied. The reactor was partially filled with water to a depth which precluded the entrainment of air from the surface, and was equipped with a sparger located at the bottom of the tank which consisted of a tubular ring 10 cm in diameter with 10 equally spaced 1.0 mm holes therein. Air or nitrogen was sparged through the system at various rates expressed as volumes of gas flowing (at 25° C. and atmospheric pressure) per volume of liquid in the tank per minute (VVM). The only source of mixing was the sparging. Oxygen concentration was measured with a polarographic oxygen electrode. The tank was initially purged of all oxygen with nitrogen gas and then aerated. Oxygen transfer rate was calculated from the time course of reoxygenation using the standard technique. Pressure variations were detected with a pressure sensor (Omega, type R735101). Conditioned signals were then fed to a Hewlett Packard model 3561A Dynamic Signal Analyser adjusted to filter out all signals except those between 0.5 Hz and 3.0 Hz and adjusted to provide the RMS signal over this frequency range. In companion experiments, irrelevant frequency ranges were also measured. The results obtained are given in the following Table 1, and clearly demonstrate the importance of removing irrelevant frequencies from the measurement at both the upper and lower ends of the power spectrum.

TABLE 1

| VVM | RMS signal output | | | Oxygen transfer rate |
|---|---|---|---|---|
| | 0.25–0.5 Hz | 0.5–3.0 Hz | 10–20 Hz | |
| 2 | 17 | 5.0 | 2.0 | 3.0 |
| 1.5 | 17 | 4.8 | 2.0 | 2.5 |
| 1.0 | 17 | 4.6 | 2.0 | 1.8 |
| 0.5 | 17 | 3.1 | 2.0 | 0.8 |

Under these conditions, with a VVM of 2, mechanical agitation provided by operating the propeller at 50 rpm increased the oxygen transfer rate to 3.3, increased the output in the 0.5 to 3.0 Hz range to 7.1, while the output in the 0.25-0.5 Hz and 10 to 20 Hz ranges remained the same. For the set of data presented in Table 1, the correlation coefficient for oxygen transfer rate and output in the 0.5 to 3.0 Hz range is 0.93, indicating a very high degree of correlation between these parameters. The output in the 0.5 to 3.0 Hz range is the mixing signal in this Example. In contrast, the correlation between oxygen transfer rate and output in the 10-20 or 0.25-0.5 Hz ranges is zero.

EXAMPLE 2

A continuously stirred tank reactor with a volume of 20 liters was employed to investigate the correlation between the RMS (root mean square mixing signal) and oxygen transfer rate. In this case, a Stratham PM-131-TC pressure sensor and a Bofors BKF-1-M/C amplifier were used, with active low-pass and high-pass filters set to pass frequencies between 0.1 and 50 Hz. It had been determined in preliminary investigations that the mixing signal was obtained in this frequency range. Oxygen transfer rates were measured with a polarographic probe and standard techniques. In this set of measurements, the aeration rate was held constant at 1.0 VVM. The reactor was equipped with 3 equally spaced 6-bladed Rushton impellers; the tank was of standard dimensions (i.e. height 3 times width; impellers one third the tank diameter; four baffles one fifth the diameter of the tank). The results obtained are given in the following Table 2. The correlation coefficient between the mixing signal (MS) over the range from 0.1 Hz to 50 Hz and the oxygen transfer rate (mM/liter-hr) is 0.89, indicating a very high degree of correlation between the measured parameters.

TABLE 2

| RPM | Oxygen Transfer Rate | MS |
| --- | --- | --- |
| 100 | 35 | 0.27 |
| 200 | 67 | 0.28 |
| 300 | 92 | 0.35 |
| 400 | 110 | 0.53 |
| 500 | 128 | 0.73 |

EXAMPLE 3

Figure 2A:
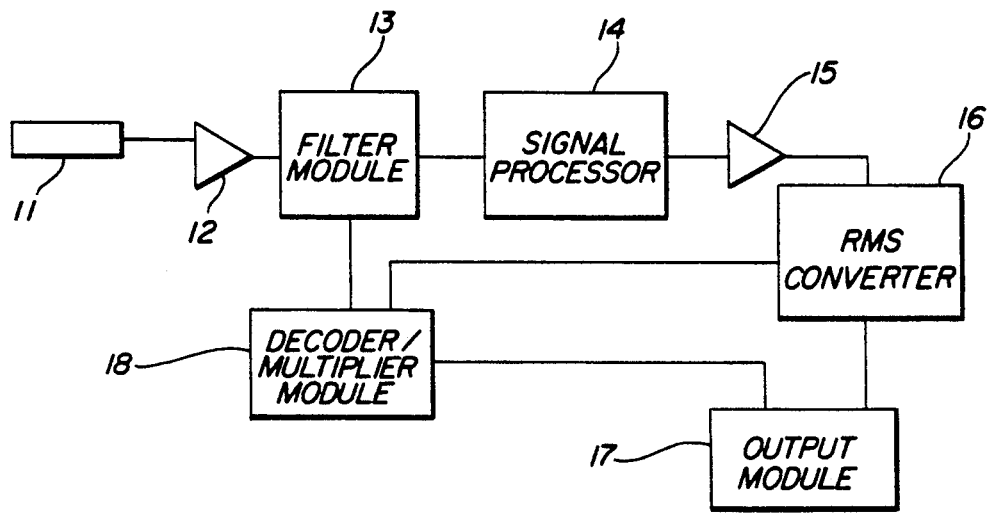
FIG. 2a is a block diagram of an embodiment of a device for performing mixing measurements.

An example of a specialized device for performing mixing measurements was designed, assembled and tested. FIG. 2a shows a block diagram of the design of the device. The signal flow in this example of the method in an electronic device is as follows:

(a) A pressure transducer 11 picks up variations in pressure caused by the turbulent flow of liquid in a continuously stirred tank reactor (not shown).

(b) An amplifier 12 conditions and amplifies the signal from the transducer 11.

(c) A filter module 13 contains active filters which are adjustable to remove unwanted frequencies either above or below the desired frequency band. Multiple filter modules could be added to combine the output from several desirable frequency bands.

(d) A signal processor 14 optionally processes the filtered signal by an amplifier which takes the logarithm or other transform of the signal. The signal is then conditioned by a conditioning amplifier 15.

(e) The conditioned signal is then fed into an RMS converter 16 which, in this case, produces the mixing signal.

(f) The mixing signal is then converted to a digital signal appropriate to a numerical display which is displayed in output module 17. An alternate signal path is to combine the information giving the limits of the desirable frequency band with the mixing signal in a decoder/multiplier module 18 to produce a mixing signal adjusted for frequency.

In this example of the method for measuring mixing in liquids, a probe assembly was designed to allow measurement of the low frequencies involved while permitting insertion of the probe into the continuously stirred tank reactor without contaminating the contents of the reactor, damaging the pressure transducer, or confounding the mixing signal with mechanical vibrations from the tank or mixing equipment.

Figure 2B:
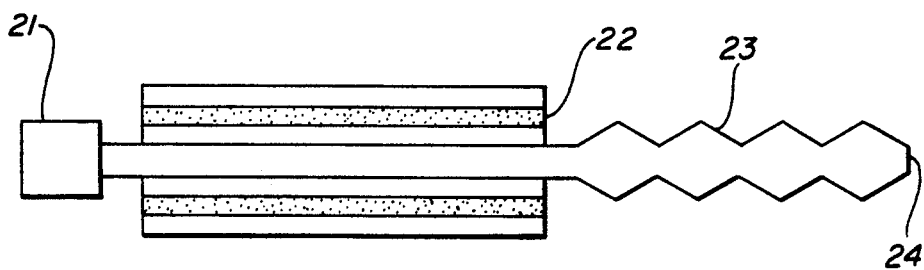

As shown in FIG. 2b, the probe assembly preferably consists of a stainless steel tube with a fitting 21 at the external end appropriate to the pressure transducer 11, a sealed flexible bellows 24 at the other, and cylindrical vibration damping 22. The flexible bellows 24 was also made of stainless steel, but could be of any appropriate material. In order that the bellows 24 be sensitive to low frequency variations, it is preferably either easily compressible or flexible along its longitudinal axis. In order that the probe be effectively isolated from mechanical vibration present in the tank and mixing equipment which is unrelated to the mixing, the probe is preferably protected by a cylindrical sheath 22 consisting of multiple, alternating layers of materials of significantly different density or compliance, silicone rubber and stainless steel, for instance.

Testing of this device was performed as follows. Two types of continuously stirred tank reactors were chosen. Type A was a standard design tank with an internal diameter of 30 cm, baffles and 3 Rushton impellers of 10 cm diameter. Type B was an unbaffled tank with a single 8-bladed impeller, a height to width ratio of approximately 1.5, and a diameter of 75 cm. For each type of tank, the mixing signal (RMS output for the frequency range 0.01 to 3.0 Hz) and the acid mixing time were determined. Acid mixing time is the time required for the mixing to completely dilute an aliquot of acid which had been added abruptly to the top of the tank, and is the time required for a pH electrode inserted into the tank near its bottom to reach 95% of its final value after the acid has been added. The acid mixing time is a measure of the effectiveness of the mixing system to disperse, dilute and partially neutralize the acid, and is an example of a simple chemical reaction.

The following Table 3a gives the results obtained with the Type A tank. For all measurements, the aeration rate was held constant at 0.4 VVM. Mixing time is the acid mixing time, and is expressed in seconds. The shorter the mixing time, the more effective the mixing. MS is the mixing signal obtained with the device described above. The correlation between mixing time and MS in the 0.01 to 3.0 Hz band is $-0.93$, indicating that there is a very close correspondence between the rate of dispersion and dilution of the acid and the mixing signal. The negative sign indicates that the mixing time decreases as the mixing signal increases.

The subsequent Table 3b gives the results obtained with the Type B tank. The type of data obtained was the same as for the Type A tank. The correlation between the direct measurement of mixing made by acid addition, the mixing time, and the mixing signal obtained with the device described above is $-0.94$, indicating a very close correspondence between these parameters, and indicating that measurements of the mixing signal within an appropriately selected band provides an appropriate means for the measurement of mixing.

In the Type A tank, a measurement of relative power input was also made. This correlates well with the mixing signal (Table 3a). This set of data provides evidence that the mixing signal is related to the power input to the mixing system, as would be expected.

TABLE 3a

| RPM | Mixing Time | MS | Relative Power |
| --- | --- | --- | --- |
| 100 | 28 | 2 | 0.03 |
| 150 | 25 | 3 | 0.12 |
| 250 | 23 | 6 | 0.20 |
| 325 | 22 | 8 | 0.90 |
| 475 | 20 | 19 | 1.80 |
| 650 | 18 | 31 | 8.00 |
| 800 | 16 | 32 | 10.50 |

TABLE 3b

| RPM | Mixing Time | MS |
| --- | --- | --- |
| 100 | 24 | 0.1 |
| 150 | 20 | 2 |
| 250 | 18 | 5 |
| 325 | 14 | 7 |
| 475 | 14 | 14 |
| 650 | 11 | 18 |
| 800 | 11 | 17 |

EXAMPLE 4

The effects of RPM and impeller design on mixing in a biochemical reactor were also studied. In this study, the chemical reactor used was an NLF-22 fermentor (Bioengineering AG., Switzerland) equipped with two 6-bladed turbine impellers approximately one-third the diameter of the 20 liter vessel. Oxygen transfer rates were used as a direct measure of the degree of chemical mixing in the reactor. Mixing signals were measured with a sealed stainless steel pressure transducer (Cole-Parmer, Inc.) and signal analysis was performed with a Hewlett Packard 3561A Dynamic Signal Analyser. Power spectra were taken as the average of 25 records, each of 2.5 seconds duration. The mixing signal was taken as the intensity of the signal averaged over the frequency range of from 2 to 40 Hz.

Without airflow, the mixing signal increased monotonically as RPM were increased from 250 to 1200 RPM (Table 4a). In a second series of measurements, air flow was maintained constant, and RPM were increased over the same range. Measurements were made at the indicated mixing signals. For each air flow rate, the rate of oxygen transfer was a monotonic function of the mixing signal (Table 4b). As the relative contributions of airflow and mechanical mixing to the mixing signal were not determined, it is to be expected that a particular mixing signal does not correspond to a particular oxygen transfer rate determined under other conditions.

Measurements of the mixing signal in frequency bands either below or above the 2 to 40 Hz band had no relation to the measured oxygen transfer rates.

Impeller design was modified by changing the angle of the impeller blades with respect to the direction of rotation. The normal angle is 90 degrees; the modified angles were 60, 45, 10 and 5 degrees. Impellers with angled blades were then used in studies of the relationship between the mixing signal and the oxygen transfer rate. In Table 4c, data are presented which show the relationship between the mixing signal and the oxygen transfer rate for measurements made with an RPM of 500 and an air flow rate of 0.5 VVM.

In summary, the results of this example demonstrate that the mixing signal is an effective indicator of the rate of a physicochemical reaction in another type of chemical reactor, namely a fermentor, and that it also is a measure of reaction rate with non-standard mixing equipment.

TABLE 4a

| RPM | Mixing Signal |
| --- | --- |
| 250 | 1.0 |
| 500 | 2.0 |
| 750 | 2.5 |
| 1200 | 3.1 |

TABLE 4b

| Air Flow Rate (VVM) | Mixing Signal | Oxygen Transfer Rate |
| --- | --- | --- |
| 0.25 | 1 | 1.5 |
|  | 3 | 4.0 |
|  | 5 | 10.0 |
| 0.5 | 1 | 4.0 |
|  | 3 | 9.0 |
|  | 5 | 15.0 |
| 0.75 | 1 | 9.5 |
|  | 3 | 16.0 |
|  | 5 | 20.0 |
| 1.0 | 1 | 14.0 |
|  | 3 | 19.0 |
|  | 5 | 23.0 |

TABLE 4c

| Blade Angle | Mixing Signal | Oxygen Transfer Rate |
| --- | --- | --- |
| 90 degrees | 5.8 | 18.0 |
| 60 | 5.4 | 16.3 |
| 45 | 4.5 | 13.3 |
| 10 | 3.0 | 8.0 |
| 5 | 1.0 | 5.7 |

The high correlations between direct chemical measures of mixing and the results of the method described herein indicate the practical value of the method of the invention. Although the mixing signals were obtained in quite different mixing situations with quite diverse sets of equipment, the results demonstrate that careful selection of a frequency band can give an instrumental measure of mixing which is an appropriate measure of those aspects of the mixing process which affect the rate of chemical and physicochemical processes.

The embodiments of the invention in which an exclusive property or privilege is claimed are defined as follows:

1. A method of measuring the degree of mixing in a turbulent liquid system, which comprises:
   (a) inserting into the liquid system a probe capable of responding to variations in a chemical or physical parameter which can vary in said system,
   (b) electronically processing a signal from said probe by amplifying the signal from the probe, filtering the signal to remove unwanted frequency ranges and converting the filtered signal to a readable output consisting of a power spectrum over a specified frequency range or to a transformed single numerical output, and
   (c) comparing said output with a calibrated range so as to enable the mixing process to be monitored or optimized.

2. A method according to claim 1, wherein the probe responds to variations in pressure, velocity, acceleration, chemical concentration or temperature in said liquid system or to any combination thereof.

3. A method according to claim 2, wherein the probe responds to variations in pressure.

4. A method according to claim 1, wherein the probe is capable of responding to a variation in a parameter within an appropriate subset of frequencies in the frequency range of about 0.01 Hz to 10 MHz.

5. A method according to claim 4, wherein the subset of frequencies is between about 0.01 Hz and 1000 Hz.

6. A method according to claim 5, wherein the subset of frequencies is between about 0.5 Hz and 3.0 Hz.

7. A method according to claim 5, wherein the subset of frequencies is between about 0.01 Hz and 3.0 Hz.

8. A method according to claim 5, wherein the subset of frequencies is between about 2 Hz and 40 Hz.

9. A method according to claim 5, wherein the probe responds to variations in pressure.

10. A method according to claim 4, wherein the signal is filtered to remove unwanted frequency ranges with a high pass filter having a cutoff frequency between about 0.001 and 1.0 Hz and a low pass filter having a cutoff frequency between about 10 Hz and 10 MHz.

11. A method according to claim 1, wherein the transformed single numerical output is a voltage or current output appropriate to the input of a recording device or computer.

12. A method according to claim 11, wherein the transformed single numerical output is RMS, logRMS, or RMS of the log of the filtered signal.

13. An apparatus for measuring the degree of mixing in a turbulent liquid system, which comprises:
(a) probe means capable of responding to variations in a chemical or physical parameter in a liquid system,
(b) processing means adapted to amplify a signal from the probe, filter the signal to remove unwanted frequencies and convert the signal to a power spectrum over a specified frequency range or to a transformed single numerical output,
(c) display means for displaying a readable output obtained from said processing means, and
(d) means for comparing said output with a calibrated range for monitoring or optimizing mixing or reaction conditions in the liquid system.

14. An apparatus according to claim 13, wherein said probe means is adapted to respond to variations in pressure, velocity, acceleration, concentration or temperature in said liquid system, or to any combination thereof.

15. An apparatus according to claim 14, wherein said probe means is adapted to respond to variations in pressure.

16. An apparatus according to claim 13, wherein the processing means comprises a high pass filter having a cutoff frequency between about 0.001 and 1.0 Hz and a low pass filter having a cutoff frequency between about 10 Hz and 10 MHz.

17. An apparatus according to claim 13, further comprising means for producing a transformed single numerical output as a voltage or current output appropriate to the input of a recording device or computer.

18. An apparatus according to claim 17, wherein the transformed single numerical output is RMS, logRMS, or RMS of the log of the filtered signal.

19. An apparatus according to claim 14, wherein the processing means is adapted to modify the mixing signal output according to the frequency range or ranges appropriate to the determination of the mixing signal.

20. An apparatus for measuring the degree of mixing in a turbulent liquid system, which comprises:
(a) probe means capable of responding to variations in a chemical or physical parameter in a liquid system, wherein said probe means comprises
  (i) a pressure transducer and
  (ii) a probe penetration device adapted to provide greatest responsiveness over the frequency range appropriate to measurement of the mixing signal by transmitting low frequency vibrations in said turbulent liquid system to said pressure transducer, said probe penetration device comprising a sealed bellows or nipple that is flexible along its longitudinal axis,
(b) processing means for electronically transforming a signal from said probe to a readable output,
(c) display means for displaying a readable output obtained from said processing means, and
(d) means for comparing said output with a calibrated range for monitoring or optimizing mixing or reaction conditions in the liquid system.

21. An apparatus according to claim 20, wherein said probe means further comprises:
(c) means for isolating the probe means from mechanical vibration which is unrelated to the mixing, comprising a cylindrical sheath consisting of a plurality of layers of materials of significantly different density or compliance.

22. An apparatus according to claim 21, wherein said cylindrical sheath consists of a layer of silicone rubber and a layer of stainless steel.

* * * * *